(12) United States Patent
Lamontia et al.

(10) Patent No.: US 10,892,588 B2
(45) Date of Patent: Jan. 12, 2021

(54) ELECTRICAL CONNECTIONS FOR WEARABLES AND OTHER ARTICLES

(71) Applicant: E I DU PONT DE NEMOURS AND COMPANY, Wilmington, DE (US)

(72) Inventors: Mark Allan Lamontia, Landenberg, PA (US); Joseph James Duffy, Newark, DE (US)

(73) Assignee: DUPONT ELECTRONICS, INC., Wilmington, DE (US)

( * ) Notice: Subject to any disclaimer, the term of this patent is extended or adjusted under 35 U.S.C. 154(b) by 101 days.

(21) Appl. No.: 16/244,601

(22) Filed: Jan. 10, 2019

(65) Prior Publication Data
US 2019/0148900 A1    May 16, 2019

Related U.S. Application Data

(63) Continuation-in-part of application No. 15/825,278, filed on Nov. 29, 2017, now abandoned.

(60) Provisional application No. 62/428,763, filed on Dec. 1, 2016.

(51) Int. Cl.
| | | |
|---|---|---|
| *H01R 33/94* | (2006.01) | |
| *H01R 12/77* | (2011.01) | |
| *A41B 1/08* | (2006.01) | |
| *A61B 5/00* | (2006.01) | |
| *H01L 23/538* | (2006.01) | |
| *A61B 5/024* | (2006.01) | |
| *H01B 1/20* | (2006.01) | |
| *H05K 1/03* | (2006.01) | |
| *A41D 1/00* | (2018.01) | |
| *H01R 12/65* | (2011.01) | |

(52) U.S. Cl.
CPC ............... *H01R 33/94* (2013.01); *A41B 1/08* (2013.01); *A61B 5/02438* (2013.01); *A61B 5/6805* (2013.01); *H01B 1/20* (2013.01); *H01L 23/5387* (2013.01); *H01R 12/771* (2013.01); *H05K 1/038* (2013.01); *A41B 2300/20* (2013.01); *A41B 2300/35* (2013.01); *A41D 1/005* (2013.01); *A41D 2300/20* (2013.01); *A41D 2300/50* (2013.01); *H01R 12/65* (2013.01)

(58) Field of Classification Search
CPC combination set(s) only.
See application file for complete search history.

(56) References Cited

U.S. PATENT DOCUMENTS

| | | |
|---|---|---|
| 3,130,257 A | 4/1964 | Rott |
| 3,253,324 A | 5/1966 | Friedrich et al. |
| 3,371,250 A | 2/1968 | Ross et al. |
| 3,405,382 A | 10/1968 | Wright |

(Continued)

FOREIGN PATENT DOCUMENTS

| | | |
|---|---|---|
| CN | 21253180 | 10/2018 |
| CN | 108696954 | 10/2018 |

(Continued)

*Primary Examiner* — William H. Mayo, III
*Assistant Examiner* — Krystal Robinson

(57) ABSTRACT

This invention is related to electrical connections in wearable garments and other articles that enable the transfer of electrical signals or electrical power from one site in the garment or article to another site on the garment or article by the use of an electrical conductor printed along the length of a sewable substrate which bridges the two sites.

11 Claims, 3 Drawing Sheets

(56) References Cited

U.S. PATENT DOCUMENTS

| | | | | |
|---|---|---|---|---|
| 3,571,647 A * | 3/1971 | Robinson | ............... | H05B 33/12 313/509 |
| 3,631,594 A * | 1/1972 | Dietrich | .................. | H05K 7/06 29/831 |
| 4,164,008 A * | 8/1979 | Miller | .................. | A41D 27/085 362/103 |
| 4,191,950 A * | 3/1980 | Levin | ....................... | A61B 5/04 128/886 |
| 4,308,572 A * | 12/1981 | Davidson | ........... | A44C 15/0015 362/103 |
| 4,480,293 A * | 10/1984 | Wells | .................. | A41D 27/085 362/103 |
| 4,570,206 A * | 2/1986 | Deutsch | ............. | A44C 15/0015 362/103 |
| 4,709,307 A * | 11/1987 | Branom | ................ | H05K 1/038 362/103 |
| 4,727,603 A * | 3/1988 | Howard | ............... | A41D 27/085 2/115 |
| 5,371,657 A * | 12/1994 | Wiscombe | ......... | F21V 33/0008 362/103 |
| 5,824,996 A | 10/1998 | Kochman et al. | | |
| 5,866,847 A | 2/1999 | Saka et al. | | |
| 6,674,008 B2 | 1/2004 | Nakamura | | |
| 7,097,495 B2 | 8/2006 | Sweetland | | |
| 7,308,294 B2 | 12/2007 | Hassonjee et al. | | |
| 8,340,740 B2 | 12/2012 | Holzer et al. | | |
| 8,732,866 B2 * | 5/2014 | Genz | .................. | F21V 33/0008 2/244 |
| 8,945,328 B2 * | 2/2015 | Longinotti-Buitoni | ..................... | D06M 15/564 156/234 |
| 8,948,839 B1 * | 2/2015 | Longinotti-Buitoni | ..................... | A61B 5/6807 600/382 |
| 9,913,019 B1 | 3/2018 | Supper | | |
| 2001/0025846 A1 * | 10/2001 | Kochman | ............. | H05B 3/342 219/545 |
| 2005/0103773 A1 | 5/2005 | Diemer et al. | | |
| 2005/0159028 A1 | 7/2005 | Sweetland et al. | | |
| 2005/0235482 A1 * | 10/2005 | Deaett | ..................... | H01P 11/00 29/600 |
| 2006/0179652 A1 * | 8/2006 | Petersen | ................ | H05K 3/361 29/825 |
| 2007/0127187 A1 | 6/2007 | Defusco et al. | | |
| 2008/0083740 A1 * | 4/2008 | Kaiserman | ............... | A43B 7/04 219/520 |
| 2009/0088652 A1 * | 4/2009 | Tremblay | ............ | A61B 5/6814 600/388 |
| 2010/0276497 A1 | 11/2010 | Seban et al. | | |
| 2010/0302745 A1 * | 12/2010 | Hsu | .......................... | H05K 3/32 361/749 |
| 2010/0317954 A1 * | 12/2010 | Jeong | .................. | A61B 5/6805 600/372 |
| 2011/0305006 A1 * | 12/2011 | Hehenberger | ......... | A41D 13/01 362/103 |
| 2013/0248226 A1 * | 9/2013 | Sime | ................ | A61B 5/04085 174/251 |
| 2014/0206948 A1 | 7/2014 | Romem | | |
| 2015/0157074 A1 * | 6/2015 | Trapani | ................ | A41D 27/201 2/251 |
| 2016/0161376 A1 * | 6/2016 | Myry | .................... | A61B 5/1116 702/182 |
| 2017/0027473 A1 * | 2/2017 | Lai | ........................ | A61B 5/7278 |
| 2017/0086513 A1 * | 3/2017 | Maxey | .................... | H05K 3/303 |
| 2018/0090861 A1 * | 3/2018 | Lamontia | ............... | A41D 1/005 |
| 2018/0289082 A1 | 10/2018 | Burrows et al. | | |
| 2018/0368213 A1 | 12/2018 | Lamontia et al. | | |

FOREIGN PATENT DOCUMENTS

| | | |
|---|---|---|
| CN | 109104777 | 12/2018 |
| DE | 102018002686 | 10/2018 |
| JP | 2018-178349 | 11/2018 |

* cited by examiner

ELECTRICAL CONNECTIONS FOR WEARABLES AND OTHER ARTICLES

FIELD OF THE INVENTION

This invention is directed to electrical connections in wearable garments and other articles to enable the transfer of electrical signals from one part of the garment to another part.

BACKGROUND OF THE INVENTION

There is increasing interest in incorporating electrical circuits in wearable garments to monitor physiological aspects of the wearer. Examples of such measurements include heart rate, electrocardiography, skin or core temperature and parameters of bodily fluids. These electrical circuits are also useful for adding energy to power devices such as heaters to increase comfort or for adding information to contained devices. These electrical circuits are also useful for articles, e.g., sleeping bags and blankets, requiring stretchable circuits. Additional uses for circuits in wearable garments and other articles are also contemplated. There is a need for methods of transferring electrical signals from one part of the wearable garment or article to another part and therefore a need for making electrical connections between different parts of the garment or article. These connections must be maintained as the garment or article is stretched and exposed to multiple wash and dry cycles.

SUMMARY OF THE INVENTION

This invention provides electrical connections in wearable garments and other articles to enable the transfer of electrical signals or electrical power from different sites of the garment or the articles.

The invention provides an electrical connection from an electrical conductor inside a wearable garment to a designated site on the outer side of the garment, the connection comprising:

an electrical conductor printed along the length of a bridging sewable substrate, wherein one end of the bridging sewable substrate is placed such that the printed conductor at that end of the bridging sewable substrate is in contact with the electrical conductor inside the garment, wherein one or more stitches with non-conductive thread are sewn through the bridging sewable substrate with each stitch encompassing the portions of the two electrical conductors that are in contact, thereby providing the compression necessary to form an electrical connection between the two conductors and wherein the other end of the bridging sewable substrate is placed at the designated site.

In one such embodiment, the end of the bridging sewable substrate at the designated site has been passed through an opening in the garment that provides access to the designated site so that the bridging sewable substrate overlaps the outer side of the garment as it approaches the designated site.

In another such embodiment, the end of the bridging sewable substrate at the designated site has been passed through a seam in the garment that provides access to the designated site so that the bridging sewable substrate overlaps the outer side of the garment as it approaches the designated site.

In still another such embodiment, the end of the bridging sewable substrate at the designated site has been folded around the edge of the garment, i.e., the end of a sleeve or a collar or the top or bottom of the garment, so that the bridging sewable substrate overlaps the outer side of the garment as it approaches the designated site.

In any of the above embodiments, the electrical conductor inside the garment is a wire.

In any of the above embodiments, the electrical conductor inside the garment is an electrical conductor printed on a sewable substrate and the one or more stitches are sewn through both sewable substrates The invention also provides an electrical connection from a first site on an article to a second site on the article.

DETAILED DESCRIPTION OF THE INVENTION

Figure 1:
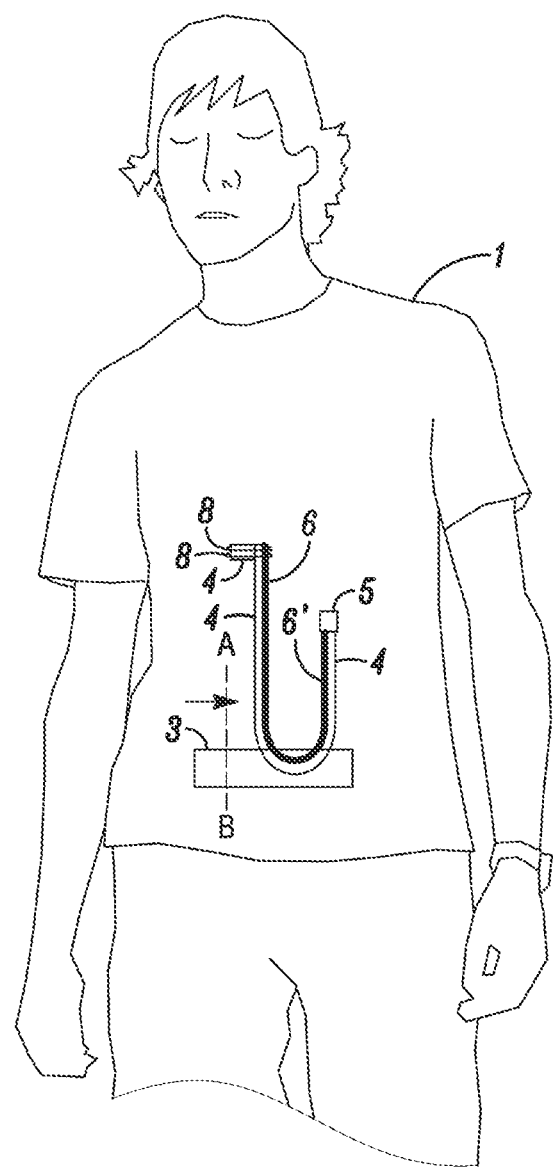
FIG. 1 illustrates an electrical connection from an electrical conductor inside a garment to a designated site on the outer side of the garment wherein the bridging sewable substrate with the printed electrical conductor along its length has one end in contact with the conductor inside the garment and the other end at the designated site and the bridging sewable substrate passes through an opening in the garment to the designated site on the outer side of the garment.

The invention relates to electrical connections in wearable garments or other articles to enable the transfer of electrical signals or power from one part of a garment or article to another.

This invention provides an electrical connection from an electrical conductor inside a wearable garment to a designated site on the outer side of the garment, the connection comprising an electrical conductor printed along the length of a bridging sewable substrate, wherein one end of the bridging sewable substrate is placed such that the printed conductor at that end of the bridging sewable substrate is in contact with the electrical conductor inside the garment, wherein one or more stitches with non-conductive thread are sewn through the bridging sewable substrate with each stitch encompassing the portions of the two electrical conductors that are in contact, thereby providing the compression necessary to form an electrical connection between the two conductors and wherein the other end of the bridging sewable substrate is placed at the designated site. In some embodiments the designated site is in a pocket of the garment or in a flap or folded flap on the garment. The garment in these embodiments can be a single layer or a multi-layer garment. In some embodiments the electrical conductor inside the garment may be a wire. In other embodiments. the electrical conductor inside the garment is an electrical conductor printed on a sewable substrate and the one or more stitches are sewn through both sewable substrates.

A wearable garment has an inner surface or side nearest to the body of the wearer and an outer surface or side farthest from the body of the wearer. As used herein, "an electrical conductor inside the garment" refers to an electrical conductor in the region between the body of the wearer and the inner surface of the garment. The electrical conductor may be attached to the body of the wearer or be attached to the inner surface of the garment or be attached to an electrical circuit in the region between the body of the wearer and the inner surface of the garment.

As used herein, "bridging substrate" refers to the substrate with the electrical conductor printed along its length, the substrate bridging the gap between a first site and a second site or between the electrical conductor inside the garment and the designated site on the outer side of the garment.

As used herein, "flap" refers to a projecting or hanging piece attached to the outer side of the garment. The flap may be folded to form a "folded flap" that provides an enclosure for the designated site and any attachments to it.

As used herein, "wearable garment" or "wearable" refers to any article that may be worn by a person and includes a shirt, a sweater, a coat or jacket, a pair of slacks, socks, and footwear.

As used herein, "lamination" refers to the bonding of two layers together. This can be accomplished by the typical process of heat and compressing the layers but also by other means such as the use of an adhesive or gluing.

Some of the above embodiments will be discussed with reference to the Figures. In the Figures, prime numbers are used to indicated the portions of the bridging sewable substrate and the electrical conductor printed along its length that lie outside the garment and un-primed numbers are used to indicated the portions of the bridging sewable substrate and the electrical conductor printed along its length that lie inside the garment.

FIG. 1 illustrates an electrical connection from an electrical conductor inside a garment to a designated site on the outer side of the garment wherein the bridging sewable substrate with the printed electrical conductor along its length has one end in contact with the conductor inside the garment and the other end at the designated site and the bridging sewable substrate passes through an opening in the garment to the designated site on the outer side of the garment. The garment 1 has an opening 3 in the garment 1. There is the electrical conductor 4 inside the garment and the designated site 5 on the outer side of the garment. Inside the garment, the bridging sewable substrate 6 with the electrical conductor 4 printed along its length is shown beginning at the electrical conductor 4 and proceeding to the opening 3. The bridging sewable substrate with the electrical conductor printed along its length passes through the opening 3. On the outer side of the garment, the bridging sewable substrate 6' with the electrical conductor 4 printed along its length terminates at the designated site 5. Two stitches of non-conductive thread 8 are sewn through the bridging sewable substrate 6 with each stitch encompassing the portions of the two electrical conductors 4 and 4 that are in contact.

Figure 2:
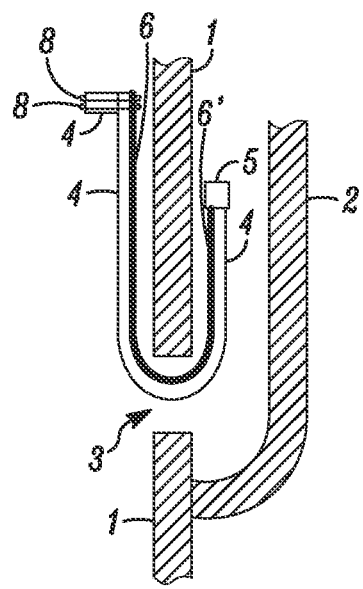
FIG. 2 is a cross-sectional view of an electrical connection from an electrical conductor inside the garment to a designated site in a pocket on the outer side of the garment wherein the bridging sewable substrate with the printed electrical conductor along its length has one end in contact with the conductor inside the garment and the other end at the designated site and the bridging sewable substrate passes through an opening in the garment to the designated site in the pocket on the outer side of the garment.

FIG. 2 is a cross-sectional view through plane AB of FIG. 1 of an electrical connection from an electrical conductor inside a garment to a designated site in a pocket on the outer side of the garment wherein the bridging sewable substrate with the printed electrical conductor along its length has one end at the electrical conductor inside the garment and the other end at the designated site and the bridging sewable substrate passes through an opening in the garment to the designated site in the pocket on the outside of the garment. The garment 1 has a pocket 2 and an opening 3 in the garment 1. There is the electrical conductor 4 inside the garment and the designated site 5 on the outer side of the garment in the pocket 2. Inside the garment, the bridging sewable substrate 6 with the electrical conductor 4 printed along its length is shown beginning at the electrical conductor 4 and proceeding to the opening 3. The bridging sewable substrate with the electrical conductor printed along its length passes through the opening 3. On the outer side of the garment, the bridging sewable substrate 6' with the electrical conductor 4 printed along its length terminates at the designated site 5 in the pocket 2. Two stitches of non-conductive thread 8 are sewn through the bridging sewable substrate 6 with each stitch encompassing the portions of the two electrical conductors 4 and 4 that are in contact.

Figure 3:
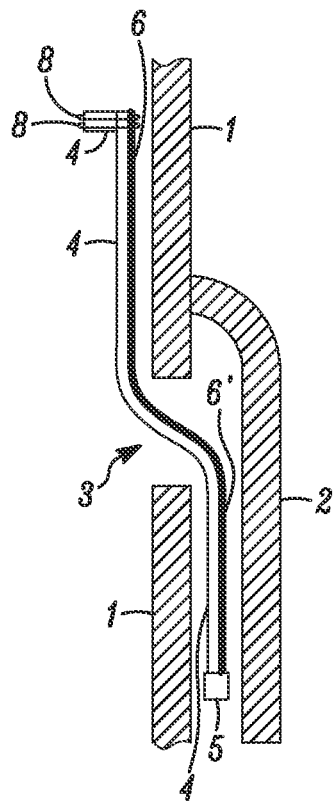
FIG. 3 is a cross-sectional view of an electrical connection from an electrical conductor inside the garment to a designated site in a flap on the outer side of the garment wherein the bridging sewable substrate with the printed electrical conductor along its length has one end in contact with the conductor inside the garment and the other end at the designated site and the bridging sewable substrate passes through an opening in the garment to the designated site in the flap on the outer side of the garment.

FIG. 3 is a cross-sectional view through plane AB of FIG. 1 of an electrical connection from an electrical conductor inside a garment to a designated site in a flap on the outer side of the garment wherein the bridging sewable substrate with the printed electrical conductor along its length has one end at the electrical conductor inside the garment and the other end at the designated site and the bridging sewable substrate passes through an opening in the garment to the designated site in the flap on the outside of the garment. The garment 1 has a flap 2 and an opening 3 in the garment 1. There is the electrical conductor 4 inside the garment and the designated site 5 on the outer side of the garment in the flap 2. Inside the garment, the bridging sewable substrate 6 with the electrical conductor 4 printed along its length is shown beginning at the electrical conductor 4 and proceeding to the opening 3. The bridging sewable substrate with the electrical conductor printed along its length passes through the opening 3. On the outer side of the garment, the bridging sewable substrate 6' with the electrical conductor 4 printed along its length terminates at the designated site 5 in the flap 2. Two stitches of non-conductive thread 8 are sewn through the bridging sewable substrate 6 with each stitch encompassing the portions of the two electrical conductors 4 and 4 that are in contact.

Figure 4:
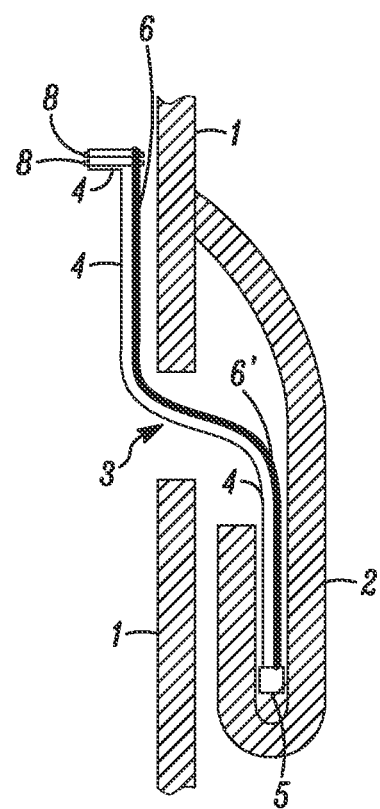
FIG. 4 is a cross-sectional view of an electrical connection from an electrical conductor inside the garment to a designated site in a folded flap on the outer side of the garment wherein the bridging sewable substrate with the printed electrical conductor along its length has one end in contact with the conductor inside the garment and the other end at the designated site and the bridging sewable substrate passes through an opening in the garment to the designated site in the folded flap on the outer side of the garment.

FIG. 4 is a cross-sectional view through plane AB of FIG. 1 of an electrical conductor inside the garment to a designated site in a folded flap on the outer side of the garment wherein the bridging sewable substrate with the printed electrical conductor along its length has one end at the electrical conductor inside the garment and the other end at the designated site and the bridging sewable substrate passes through an opening in the garment to the designated site in the folded flap on the outside of the garment. The garment 1 has a folded flap 2 and an opening 3 in the garment 1. There is the electrical conductor 4 inside the garment and the designated site 5 on the outer side of the garment in the folded flap 2. Inside the garment, the bridging sewable substrate 6 with the electrical conductor 4 printed along its length is shown beginning at the electrical conductor 4 and proceeding to the opening 3. The bridging sewable substrate with the electrical conductor printed along its length passes through the opening 3. On the outer side of the garment, the bridging sewable substrate 6' with the electrical conductor 4 printed along its length terminates at the designated site 5 in the folded flap 2. Two stitches of non-conductive thread 8 are sewn through the bridging sewable substrate 6 with each stitch encompassing the portions of the two electrical conductors 4 and 4 that are in contact.

Embodiments with the bridging substrate passing through a seam would be similar to those illustrated in FIGS. 1, 2, 3 and 4 with a seam replacing the opening 3.

As shown in FIG. 1, the bridging substrate 6 and 6' is adjacent to the garment 1 both inside and outside the garment and the electrical conductor 4 and 4 is exposed making connections at the electrical conductor 4 inside the garment 1 and the designated site 5 outside the garment 1 convenient. The bridging substrate can be reversed so that the electrical conductor 4 and 4 is adjacent to the garment 1 both inside and outside the garment thereby providing the electrical conductor 4 and 4 protection from abrasion. For embodiments in which the bridging substrate with the printed electrical conductor consists of two separate pieces of substrate each with an electrical conductor printed along its length, the two substrates can be placed so that the bridging substrate is adjacent to the garment on one side of the garment and the electrical conductor is adjacent to the garment on the other side. Similar reversals or combinations of two separate pieces of substrate are applicable to all embodiments.

In any of the above embodiments, the bridging substrate may comprise thermoplastic or thermoset films. Examples of typical substrates are thermoplastic urethane (TPU) such as Bemis ST-604 available from Bemis Associates, Inc., Shirley, Mass., thermoplastic polyester such as DuPont™ Hytrel® available from the DuPont Co., Wilmington, Del., thermoplastic polyethylene terephthalate (PET) and DuPont™ Kapton® polyimide available from the DuPont Co., Wilmington, Del.

In any of the above embodiments, the electrical conductor printed along the length of the bridging sewable substrate may be formed from a polymer thick film conductor composition.

In any of the above embodiments, the electrical conductor printed along the length of the bridging sewable substrate may be formed from a polymer thick film silver composition.

In any of the above embodiments, the electrical connection may further comprise one or more additional electrical conductors printed along the length of the bridging sewable substrate.

In any of the above embodiments, the bridging sewable substrate with the printed electrical conductor may consist of two or more separate pieces of sewable substrate each with an electrical conductor printed along its length and wherein the printed conductors of neighboring pieces of sewable substrate are placed in contact and the electrical connection of the printed electrical conductors on the two or more pieces of substrate is achieved by means of:

a) stitches with non-conductive thread, wherein each stitch is sewn through the neighboring sewable substrates and wherein each pair of contacted conductors is encompassed by at least one stitch, thereby providing the compression necessary to form an electrical connection of each pair; or b) lamination of two neighboring pieces of substrate; or c) fasteners compressing the two neighboring pieces of substrate together.

What is claimed is:

1. An electrical connection from an electrical conductor inside a wearable garment to a designated site on an outer side of the garment, the connection comprising:

a printed conductor along the length of a bridging sewable substrate, wherein one end of the bridging sewable substrate is placed such that the printed conductor at that end of the bridging sewable substrate is in contact with the electrical conductor inside the garment, wherein one or more stitches with non-conductive thread are sewn through the bridging sewable substrate with each stitch encompassing the portions of the two electrical conductors that are in contact with the bridging sewable substrate, thereby providing the compression necessary to form an electrical connection between the two conductors and wherein the other end of the bridging sewable substrate is placed at the designated site on the outer side of the garment, wherein the outer side of the garment is an outer surface, wherein the end of the bridging sewable substrate at the designated site on the outer surface of the garment has been passed through an opening in the garment that provides access to the designated site on the outer surface of the garment so that the bridging sewable substrate overlaps the outer side of the garment as it approaches the designated site on the outer surface of the garment.

2. The electrical connection of claim 1, wherein the electrical conductor inside the garment is a wire.

3. The electrical connection of claim 1, wherein the wearable garment is a single layer garment.

4. The electrical connection of claim 1, wherein the wearable garment is a multi-layer garment.

5. The electrical connection of claim 1, the bridging sewable substrate comprising thermoplastic urethane.

6. The electrical connection of claim 1, wherein the electrical conductor printed along the length of the bridging sewable substrate is formed from a polymer film conductor composition.

7. The electrical connection of claim 6, wherein the polymer film conductor composition is a polymer thick film silver composition.

8. The electrical connection of claim 1, the electrical connection further comprising one or more additional electrical conductors printed along the length of the bridging sewable substrate.

9. An electrical connection from an electrical conductor inside a wearable garment to a designated site on an outer side of the garment, the connection comprising:

a printed conductor along the length of a bridging sewable substrate, wherein one end of the bridging sewable substrate is placed such that the printed conductor at that end of the bridging sewable substrate is in contact with the electrical conductor inside the garment, wherein one or more stitches with non-conductive thread are sewn through the bridging sewable substrate with each stitch encompassing the portions of the two electrical conductors that are in contact with the bridging sewable substrate, thereby providing the compression necessary to form an electrical connection between the two conductors and wherein the other end of the bridging sewable substrate is placed at the designated site on the outer side of the garment, wherein the outer side of the garment is an outer surface, wherein the end of the bridging sewable substrate at the designated site on the outer surface of the garment has been passed through a seam in the garment that provides access to the designated site on the outer surface of the garment so that the bridging sewable substrate overlaps the outer side of the garment as it approaches the designated site on the outer surface of the garment.

10. An electrical connection from an electrical conductor inside a wearable garment to a designated site on an outer side of the garment, the connection comprising:

a printed conductor along the length of a bridging sewable substrate, wherein one end of the bridging sewable substrate is placed such that the printed conductor at that end of the bridging sewable substrate is in contact with the electrical conductor inside the garment, wherein one or more stitches with non-conductive thread are sewn through the bridging sewable substrate with each stitch encompassing the portions of the two electrical conductors that are in contact with the bridging sewable substrate, thereby providing the compression necessary to form an electrical connection between the two conductors and wherein the other end of the bridging sewable substrate is placed at the designated site on the outer side of the garment, wherein the outer side of the garment is an outer surface, wherein the end of the bridging sewable substrate at the designated site on the outer surface of the garment has been folded around an edge of the garment so that the bridging sewable substrate overlaps the outer side of the garment as it approaches the designated site on the outer surface of the garment.

11. An electrical connection from an electrical conductor inside a wearable garment to a designated site on an outer side of the garment, the connection comprising:

a printed conductor along the length of a bridging sewable substrate, wherein one end of the bridging sewable substrate is placed such that the printed conductor at that end of the bridging sewable substrate is in contact with the electrical conductor inside the garment, wherein one or more stitches with non-conductive thread are sewn through the bridging sewable substrate with each stitch encompassing the portions of the two electrical conductors that are in contact with the bridging sewable substrate, thereby providing the compression necessary to form an electrical connection between the two conductors and wherein the other end of the bridging sewable substrate is placed at the designated site on the outer side of the garment, wherein the outer side of the garment is an outer surface, wherein the bridging sewable substrate with the printed electrical conductor consists of two or more separate pieces of sewable substrate each with an electrical conductor printed along its length and wherein the printed conductors of neighboring pieces of substrate are placed in contact and the electrical connection of the printed electrical conductors on the two or more pieces of substrate is achieved by means of:

a) stitches with non-conductive thread, wherein each stitch is sewn through the neighboring sewable substrates and wherein each pair of contacted conductors is encompassed by at least one stitch, thereby providing the compression necessary to form an electrical connection of each pair; or b) lamination of two neighboring pieces of substrate; or c) fasteners compressing the two neighboring pieces of substrate together.

* * * * *